United States Patent [19]

Yamada et al.

[11] Patent Number: 5,556,999
[45] Date of Patent: Sep. 17, 1996

[54] ALKOXYSILANE COMPOSITION INHIBITED FROM DISPROPORTIONATION REACTION

[75] Inventors: Yoshinori Yamada; Mitsutaka Hasegawa; Katsuyoshi Harada, all of Nagoya, Japan

[73] Assignee: Toagosei Co., Ltd., Tokyo, Japan

[21] Appl. No.: 556,003

[22] Filed: Nov. 13, 1995

[30] Foreign Application Priority Data

Nov. 14, 1994 [JP] Japan .................................... 6-304419

[51] Int. Cl.⁶ .................................. C07F 7/08; C07F 7/18
[52] U.S. Cl. ........................................................... 556/401
[58] Field of Search ............................................. 556/401

[56] References Cited

U.S. PATENT DOCUMENTS 3,948,964  4/1976  Barfurth et al. ...................... 556/401
4,921,987  5/1990  Hitze et al. ........................... 556/401

FOREIGN PATENT DOCUMENTS 64-90192  6/1989  Japan .

Primary Examiner—Paul F. Shaver
Attorney, Agent, or Firm—Cushman Darby & Cushman, L.L.P.

[57] ABSTRACT

Alkoxysilane composition, which is inhibited from disproportionation reaction that may cause production of monosilanes or reduction in purity of products, contains an alkoxysilane represented by the formula [I] and substantially free from alcohols:

$$H_m R_n Si(OR')_{4-m-n} \quad \text{[I]}$$

wherein m is an integer of 1–3, n is an integer of 0–2, $m+n \leq 3$, R is a $C_1$-$C_8$ alkyl group, and R' is a $C_1$-$C_4$ alkyl group, with a proviso that when there are two or more R or R', R and R' may be the same or different respectively, and at least one compound selected from the group consisting of organic sulfonic acids, sulfuric acid, $SO_2$, carboxylic acids, carboxylic anhydrides and $CO_2$.

4 Claims, No Drawings

ALKOXYSILANE COMPOSITION INHIBITED FROM DISPROPORTIONATION REACTION

The present invention provides an alkoxysilane composition inhibited from disproportionation reaction which may cause decrease in purity of alkoxysilanes and produce monosilanes.

Alkoxysilanes having a hydrogen and an alkoxyl group represented by the formula [I] which is hereinafter referred to as merely "alkoxysilanes":

$$H_m R_n Si(OR')_{4-m-n} \quad [I]$$

wherein m is an integer of 1–3, n is an integer of 0–2, m+n≦3, R is a $C_1$-$C_8$ alkyl group, and R' is a $C_1$-$C_4$ alkyl group, with a proviso that when there are two or more R or R', R and R' may be the same or different, respectively, have been used as materials for silane coupling agents or strong reducing agents, and, recently, as materials of semiconductors.

It is known that, when these alkoxysilanes contain alcohols, one of materials therefor, they undergo dehydrogenation reaction until quality decreases. On the other hand, purified alkoxysilanes substantially free from alcohols have been considered to undergo no such reaction as mentioned above and to be stable.

However, it has been found that when alkoxytitaniums or platinum group metals co-exist, alkoxysilanes cause disproportionation reaction with the result that purity of the alkoxysilane decreases. Furthermore, it has been found that the alkoxysilanes of the above formula [I] where m is 1–3 and n is 0, namely, containing no alkyl group of R, have large possibility of causing the disproportionation reaction mentioned above, with the result that monosilanes are produced to give various adverse influences.

Trialkoxysilanes or dialkoxysilanes among the above alkoxysilanes having the formula [I] where m is 1 or 2 and having no alkyl group come to be noticed as electronic materials such as insulation films of semiconductors, because they are supposed to be stable. However, they may be accompanied with monosilanes which would bar their applications.

On the other hand, metallic silicon which is a raw material for alkoxysilanes usually contain as impurities a small amount of metals such as titanium, calcium and aluminum. Therefore, alkoxysilanes industrially produced inevitably contain a small amount of such metals in an form of metal alkoxide as impurities. The inventors have found that such various metal alkoxides originating from the raw materials work as a catalyst which brings about disproportionation reaction of alkoxysilanes, even if there is no factor of allowing the alkoxytitanium or platinum group metals to enter the system from the outside.

One approach for inhibiting the disproportionation reaction is allowing chlorosilane to co-exist ("Canadian Journal of Chemistry", Vol.68, page 471, 1990). However, this method is not sufficiently effective. Furthermore, when alkoxysilanes are used as electronic materials, chlorine contained in chlorosilane and the like deteriorates performance of electronic parts. Therefore, silicon chlorides such as chlorosilane can hardly be used as preferable inhibitors against the disproportionation reaction of alkoxysilanes.

The present invention provides an alkoxysilane composition wherein specific compounds which are different from silicon chlorides harmful for electronic materials are allowed to be contained, with the result that the disproportionation reaction is so much controlled that production of monosilanes as well as decrease in purity of alkoxysilanes are inhibited.

According to the present invention, the disproportionation reaction and the resulting production of monosilanes can be inhibited by dissolving at least one compound selected from the group consisting of organic sulfonic acids, sulfuric acid, $SO_2$, carboxylic acids, carboxylic anhydrides and $CO_2$ in alkoxysilanes that is represented by the above formula [I] and substantially free from alcohol.

As the compounds to be added to alkoxysilanes for inhibition of the disproportionation reaction (hereinafter referred to as merely "inhibitor"), mention may be made of, for example, organic sulfonic acids such as p-toluenesulfonic acid, sulfuric acid, $SO_2$, carboxylic acids, carboxylic anhydrides such as acetic anhydride, and $CO_2$.

Of these inhibitors, organic sulfonic acids such as p-toluenesulfonic acid or $SO_2$ are better than sulfuric acid, so far as sulfur-containing compounds are concerned, because of their high inhibitory activity against the disproportionation reaction. Moreover, carboxylic anhydrides such as acetic anhydride and $CO_2$ are preferred among the compounds having a carbonyl group or carboxyl group, because of their high inhibitory activity against the disproportionation reaction.

Preferred inhibitors also depend upon use of alkoxysilanes. For example, when the presence of inhibitors in alkoxysilanes may induce any problem in use as for specific electronic materials, $CO_2$ or $SO_2$ is preferred, which are gas at room temperature and thus are able to be easily separated and removed from alkoxysilane just before use. On the other hand, for ordinary use where the presence of inhibitors are desired even when temperature increases, organic sulfonic acids, carboxylic acids or anhydrides thereof which have high boiling points are preferred. Particularly, p-toluenesulfonic acid and acetic anhydride are more preferred because of their high inhibitory effect.

Preferred amount of the inhibitor to be added to alkoxysilanes varies depending on amounts of impurities contained in the alkoxysilanes, i.e., platinum group metals, alkoxytitanium or other metal alkoxides that work as catalysts for disproportionation reaction. These impurities as a whole are hereinafter referred to as "catalytic impurities". Furthermore, inhibiting activity varies depending on kinds of inhibitors. Therefore, the amount is not generally specified, but the optimum amount would readily be determined through experiments. It is a matter of course that a large amount of inhibitors is added to alkoxysilanes containing a large amount of the catalytic impurities, and a small amount of inhibitor is enough to alkoxysilanes containing a small amount of the catalytic impurities. Generally, in the case of trialkoxysilanes or dialkoxysilanes for industrial use, which contain about several tens ppm of various catalytic impurities, amount of the inhibitor to be added is 1% to 0.1 ppm, preferably 0.5% to 1 ppm, more preferably 0.1% to 20 ppm on the basis of the amount of the alkoxysilane.

The inhibitors can usually be dissolved by just being added to or mixed with alkoxysilanes. When a gas such as $CO_2$ or $SO_2$ is used, it is bubbled in alkoxysilanes. Alternatively, the gas may be introduced into a gaseous phase in a container of alkoxysilanes to be allowed to dissolve therein.

The present invention will be explained in more detail by the following examples and comparative examples.

COMPARATIVE EXAMPLE 1

Fifty grams of triethoxysilane prepared using silicon containing metal impurities such as titanium, calcium and aluminum, which was substantially free from alcohols but contained several tens ppm of catalytic impurities of metal alkoxides originating from the above metals, were charged in a pressure cylinder of 300 ml in capacity made of a stainless steel (SUS304) under nitrogen blanket. The cylinder was kept at 100° C. for 200 hours, in order to effect an acceleration test of disproportionation reaction. Concentration of monosilane in the gaseous phase and purity of triethoxysilane in the liquid phase in the cylinder were assayed in order to examine the disproportionation reaction. The results are shown in Table 1.

EXAMPLES 1–5

Each of the inhibitors shown in Table 1 was added to the same triethoxysilanes as used in comparative example 1, and then acceleration tests were conducted using the same apparatus under the same conditions as in Comparative Example 1. The results are shown in Table 1.

Table 1 shows that purity of triethoxysilane was greatly decreased and a large amount of monosilanes was produced due to disproportionation reaction in Comparative Example 1, while no monosilanes were produced and purity of triethoxysilanes was hardly decreased in Examples 1–5. Small decreases in purity of triethoxysilane in the acceleration tests in Examples 1–5 were due to condensation reaction resulting from contamination of a very small amount of water, but disproportionation reaction was inhibited.

TABLE 1

| Inhibitor | | Concentration of inhibitor (ppm) | Purity of triethoxysilane before acceleration test | Purity of triethoxysilane after acceleration test | Concentration of monosilane after acceleration test |
|---|---|---|---|---|---|
| Comparative Example 1 | — | — | 99.0% | 86.2% | 14.4% |
| Example 1 | $SO_2$ | 100 | 99.0% | 98.8% | 0.0% |
| Example 2 | $CO_2$ | 1000 | 99.0% | 98.9% | 0.0% |
| Example 3 | Sulfuric acid | 100 | 99.0% | 96.7% | 0.0% |
| Example 4 | P-toluene-sulfonic acid | 500 | 99.0% | 98.7% | 0.0% |
| Example 5 | Acetic anhydride | 500 | 99.0% | 98.9% | 0.0% |

COMPARATIVE EXAMPLE 2

The acceleration test was conducted to examine proceeding of disproportionation reaction in the same manner as in Comparative Example 1, except that 50 g of trimethoxysilane which was prepared using silicon containing metal impurities such as titanium, calcium and aluminum and was substantially free from alcohol but contained several tens ppm of catalytic impurities of metal alkoxides originating from the above metal impurities was used, in place of the triethoxysilane (50 g). The results are shown in Table 2.

EXAMPLES 6–10

Each of the inhibitors shown in Table 2 was added to the same trimethoxysilanes used in comparative example 2, and then acceleration tests were conducted using the same apparatus under the same conditions as in Comparative Example 1. The results are shown in Table 2.

Table 2 shows that purity of trimethoxysilane was greatly decreased and a large amount of monosilanes was produced due to disproportionation reaction in Comparative Example 2, while no monosilanes were produced and purity of trimethoxysilanes was hardly decreased in Examples 6–10 of the present invention. Small decreases in purity of trimethoxysilane in the acceleration tests in Examples 6–10 were due to condensation reaction resulting from contamination of a very small amount of water, but disproportionation reaction was inhibited.

TABLE 2

| Inhibitor | | Concentration of inhibitor (ppm) | Purity of trimethoxysilane before acceleration test | Purity of trimethoxysilane after acceleration test | Concentratio of monosilane after acceleration test |
|---|---|---|---|---|---|
| Comparative Example 2 | — | — | 97.6% | 73.5% | 25.1% |
| Example 6 | $SO_2$ | 100 | 97.6% | 97.3% | 0.0% |
| Example 7 | $CO_2$ | 1000 | 97.6% | 97.4% | 0.0% |
| Example 8 | Sulfuric acid | 100 | 97.6% | 95.1% | 0.0% |
| Example 9 | P-toluene-sulfonic acid | 500 | 97.6% | 97.2% | 0.0% |
| Example 10 | Acetic anhydride | 500 | 97.6% | 97.5% | 0.0% |

COMPARATIVE EXAMPLE 3

The acceleration test was conducted to examine proceeding of disproportionation reaction in the same manner as in Comparative Example 1, except that methyldiethoxysilane (50 g) was used in place of triethoxysilane (50 g). The results are shown in Table 3.

EXAMPLE 11

$SO_2$, an inhibitor, was fed into the liquid phase of methyldiethoxysilane which was prepared from silicon containing metal impurities such as titanium, calcium and aluminum and was substantially free from alcohols but contained several tens ppm of catalytic impurities of metal alkoxides originating from the above metal impurities. Acceleration test was conducted as in Comparative Example 1 in the same apparatus under the same conditions. The results are shown in Table 3.

Table 3 shows that monosilane was not produced, but purity of methyldiethoxysilane was greatly decreased due to disproportionation reaction in Comparative Example 3. On the other hand, purity of methyldiethoxysilane was not decreased in Example 11 of the present invention, and disproportionation reaction was inhibited.

TABLE 3

| Inhibitor | | Concentration of inhibitor (ppm) | Purity of methyldiethoxysilane before acceleration test | Purity of methyldiethoxysilane after acceleration test | Concentration of monosilane after acceleration test |
|---|---|---|---|---|---|
| Comparative Example 3 | — | — | 99.6% | 92.2% | 0.0% |
| Example 11 | $SO_2$ | 100 | 99.6% | 99.6% | 0.0% |

The results of Comparative Examples 1–3 and Examples 1–11 show that the alkoxysilane compositions of the present invention have a high inhibitory activity against disproportionation reaction, with the result that production of monosilanes and decrease in purity of alkoxysilanes are effectively inhibited.

According to the present invention, an alkoxysilane composition, which is inhibited from disproportionation reaction that may cause problems such as production of monosilanes or reduction in purity of alkoxysilanes, can be obtained.

COMPARATIVE EXAMPLES 4–5

Comparative example 4 was conducted in such a manner that 25 g of triethoxysilane containing 10 ppm in total of such metal impurities as titanium, calcium and aluminum, which work as disproportionation catalysts, together with 25 g of ethanol were charged in a pressure cylinder of 300 ml in capacity made of a stainless steel (SUS304) under nitrogen blanket. The cylinder was kept at 100° C. for 200 hours, in order to effect an acceleration test of disproportionation reaction. Concentration of monosilane and purity of triethoxysilane in the cylinder were assayed in order to examine the disproportionation reaction.

In comparative example 5, comparative example 4 was repeated except that trimethoxysilane and methanol were used in place of the triethoxysilane and ethanol, respectively. The results are shown in Table 4.

TABLE 4

| | material added | concentration of material added (%) | Purity of trialkoxyoxysilane before acceleration test | Purity of trialkoxysilane after acceleration test | Concentration of monosilane after acceleration test |
|---|---|---|---|---|---|
| Comparative Example 4 | ethanol | 50.0 | 49.5% | 0.2% | 0.0% |
| Comparative Example 5 | methanol | 50.0 | 48.8% | 0.1% | 0.0% |

Comparative example 4 and 5 revealed that addition of alcohols to alkoxysilanes prevented from production of monosilanes, although purity of trialkoxysilanes after the acceleration test was decreased. In other words, when alcohols co-existed with trialkoxysilanes, conversion reaction of trialkoxysilanes into tetraalkoxysilanes preceded due to alcohol displacement, with the result that no disproportionation reaction occured. No stabilizers were necessary against disproportionation reaction, as long as alcohols were co-present. The results above showed that the present stabilization method greatly preformed inhibition from dispoporationation reaction of alkoxysilanes substantially free from alcohols, and that addition of a small amount of compounds defined above to the alkoxysilane was enough to effectively inhibit from production of monosilane and from decrease in purity of alkoxysilanes.

What is claimed is:

1. An alkoxysilane composition which comprises (a) an alkoxysilane represented by the formula [I] and substantially free from alcohols:

$$H_m R_n Si(OR')_{4-m-n} \quad [I]$$

wherein m is an integer of 1–3, n is an integer of 0–2, m+n≦3, R is a $C_1$-$C_8$ alkyl group, and R' is a $C_1$-$C_4$ alkyl group, with a proviso that when there are two or more R or R', R and R' may be the same or different respectively, and (b) at least one compound selected from the group consisting of organic sulfonic acids, sulfuric acid, $SO_2$, carboxylic acids, carboxylic anhydrides and $CO_2$.

2. An alkoxysilane composition according to claim 1, wherein the alkoxysilane is represented by the formula [I] in which m is 1 or 2, and n is 0.

3. An alkoxysilane composition according to claim 1 or 2, wherein the compound (b) is p-toluenesulfonic acid or acetic anhydride.

4. An alkoxysilane composition according to claim 2 wherein the compound (b) is contained in an amount of 1% to 0.1 ppm on the basis of alkoxysilane.

* * * * *